United States Patent [19]

Tower, Jr. et al.

[11] Patent Number: 5,218,842
[45] Date of Patent: Jun. 15, 1993

[54] APPARATUS FOR TESTING SKIS

[75] Inventors: Dell K. Tower, Jr., Plymouth; Kevin F. Ice, Concord; Robert E. Doucette, Bristol, all of N.H.

[73] Assignee: Pro-Flex, Inc., Wells, Me.

[21] Appl. No.: 973,544

[22] Filed: Nov. 9, 1992

Related U.S. Application Data

[63] Continuation of Ser. No. 672,412, Mar. 20, 1991, abandoned.

[51] Int. Cl.$^5$ .............................................. G01N 3/00
[52] U.S. Cl. .................................................. 73/794
[58] Field of Search ................ 73/794, 795, 847, 849, 73/853

[56] References Cited

U.S. PATENT DOCUMENTS

| 3,922,908 | 12/1925 | Stemsrud et al. | 73/812 |
| 3,964,300 | 6/1926 | Howe | 73/849 |
| 4,195,532 | 4/1980 | Pauls | 73/849 |
| 4,290,499 | 9/1981 | Lumaranta | 73/849 |
| 4,474,067 | 10/1984 | Cherry, III et al. | 73/794 |

FOREIGN PATENT DOCUMENTS

| 1168821 | 7/1985 | U.S.S.R. | 73/849 |

OTHER PUBLICATIONS

Standard Test Method for Center Spring Constant and Spring Constant Balance of Alpine Skis, Annual Book of ASTM Standards; 1988.
Standard Test Method for Torsion Characteristics of Alpine Skis, Annual Book of ASTM Standards, 1988.

*Primary Examiner*—Jerry W. Myracle
*Attorney, Agent, or Firm*—Robert G. Crooks

[57] ABSTRACT

According to the method of this invention, a ski to be tested is supported at its mid-point and near its tip and tail respectively. It is clamped at the mid-point and just aft of the tip of the ski. The afterbody and the forebody of the ski are deflected through predetermined distances, whereupon the force necessary to produce the deflection is measured by a strain gauge. Similarly, the forces produced in the ski when the forebody of the ski is twisted by the application of a couple thereto to produce a predetermined torsional deflection are measured and recorded. The disclosure includes a suitable tip station, center station, and tail station mounted on an elongated base, which may comprise a pair of hollow metal cylinders that act as reservoirs for storage of compressed air for actuation of pneumatic means for application of forces to the ski.

9 Claims, 5 Drawing Sheets

APPARATUS FOR TESTING SKIS

This is a continuation of copending application(s) Ser. No. 07/672,412 filed on Mar. 20, 1991, now abandoned.

This invention relates to a method and apparatus for testing skis. In particular, the invention is concerned with the evaluation of both the flexural and torsional stiffness of a ski, or skis in large quantities. These characteristics are important in matching up two skis which are sufficiently similar in stiffness characteristics to constitute a pair to be used by one person. The measurements are also important in comparing the stiffness of the forebody of each ski with the afterbody of that ski because the forebody determines the ease with which the ski will enter a turn, whereas the afterbody determines the turning characteristics once the turn has been established. Further, it is of interest to compare and contrast the various stiffness characteristics, both flexural and torsional, of pairs of skis which have been in service, with the comparable stiffness characteristics of the same skis when they were new and unused. If the skis have become "soft" with the passage of time, they may no longer be suitable for use by the persons who initially bought them.

BACKGROUND OF THE INVENTION

For many years, manufacturers and users of skis have understood that weight, length, and strength are not the only characteristics that affect the performance of the skis in action. In particular, it has become widely appreciated that the flexibility of the skis is an important factor in determining the ease with which the ski may be turned and with which a turn may be maintained by the ski once the turn has been entered. Furthermore, it is well known that the flexibility of the forebody of the ski should not necessarily be the same as the flexibility of the afterbody of the ski. Still further, it is axiomatic that both the flexural and the torsional flexibilities or stiffnesses of the skis are important. Flexural bending takes place about an axis perpendicular to the longitudinal axis of the ski, whereas torsional bending takes place about an axis substantially coincident with the longitudinal axis of the ski.

The measurements of both flexural stiffness, or spring constant, and torsional stiffness of skis are the subjects of test standards promulgated by the American Society for Testing and Materials. A *Standard Test Method for Center Spring Constant and Spring Constant Balance of Alpine Skis* was published by the American Society for Testing and Materials Committee on Standards in 1977 (Designation F-498-77-Reapproved 1988.) A *Standard Test Method for Torsion Characteristics of Alpine Skis* was published by the American Society for Testing and Materials in 1982 (Designation F-779-82-Reapproved 1988). As implied by the aforementioned titles, the thrust of those two standard test methods is a determination of spring constants, one for flexural deformation and the other of torsional deformation.

While the determination of such spring constants was a step forward, it did not provide information of the type which is most useful in the matching of skis to form a pair or in the selection of skis to conform to the preferences of individual skiers, so far as ease of entry into turns and maintenance of turns were concerned. Moreover, the procedure in accordance with those standard test methods attempted to isolate the forebody of the ski from the afterbody of the ski for the purposes of measurement. However, in use, the flexibility of the forebody and that of the afterbody influence each other because bending moments and torsional forces are transmitted between the forebody and the afterbody through the "waist" of the ski, whereon the binding is mounted and the weight of the skier is carried. Further, the data produced by the standard test methods were not so immediately useful to a person selecting skis for a pair or determining the effect of use of the skis and passage of time upon their flexural and torsional stiffness and flexibility. Accordingly, it appears that the prior art, as represented by the aforementioned standards the American Society for Testing and Materials, is deficient in one or more important ways.

OBJECTS OF THE INVENTION

In view of the deficiencies of the prior-art methods and apparatus for testing the flexural and torsional characteristics of skis, it is an object of our invention to provide a method and apparatus for quickly and conveniently obtaining a set of numbers which are truly representative of the flexibility of each ski about both transverse and longitudinal axis.

It is another object of our invention to provide quickly and conveniently a measurement of the resistance afforded by the "camber" of the ski to flattening of the ski against a level surface by the weight of the skier.

It is a further object of our invention to provide a convenient method and apparatus whereby each ski may be quickly mounted on the apparatus, tested, and removed from the apparatus within a very few minutes or even seconds.

It is a still further object of our invention to provide a method and apparatus for making such tests wherein the results of the tests will be repeatable and will not depend upon an arbitrary "zero setting" which cannot be accurately reproduced.

It is still another object of our invention to provide apparatus which is simple, inexpensive, durable, and easy for unskilled personnel to operate.

SUMMARY OF THE INVENTION

Briefly, we have fulfilled the aforementioned and other objects of our invention by providing a method and apparatus which permit and facilitate the accomplishment of the following steps:

1. Measuring the force necessary to overcome the camber of the ski;
2. Measuring the flexural stiffness of the afterbody of the ski without attempting to isolate the afterbody from forces transmitted by the forebody of the ski through the waist of the ski to the afterbody;
3. Measuring the flexural stiffness of the forebody of the ski, again without attempting to isolate the forebody from forces transmitted by the afterbody of the ski to the forebody through the waist of the ski; and
4. Measuring the torsional stiffness of the forebody of the ski, but without isolating the forebody from torsional forces transmitted thereto by the afterbody of the ski through the waist of the ski.

In the method of our invention, the ski is clamped flat upon a roll carried by a center station of the apparatus in accordance with the invention. Similarly, the low point of the ski just aft of the tip and at a leading point on the forebody of the ski is clamped to a roll at the top of a tip station in accordance with the apparatus of the invention. Although the clamp at the center station of the apparatus does not permit any rotation of the ski about the longitudinal axis of the ski, torsional forces may nevertheless by transmitted through the ski from the afterbody to the forebody and thus affect the apparent torsional stiffness of the forebody. This is a realistic way to measure torsional stiffness. When the ski is in use, both the flexural and torsional stiffnesses of the afterbody affect the apparent stiffness, flexural or torsional as the case may be, of the forebody of the ski. This method of testing in accordance with the invention contrasts with the method set forth in the aforementioned standards of the American Society for Testing and Materials, wherein a lengthy clamp is applied to the ski. Thus the forebody is tested as if it were isolated from the afterbody. Likewise, when the clamp has been moved to a point forward of the midpoint of the ski, the afterbody is tested as if it were isolated from the forebody. The method in accordance with our invention is more realistic in that it treats the ski as the ski functions in practice and allows forces to be transmitted throughout the length of the ski just as when it is in use, despite the confinement of the center point so that the ski at that point is not permitted to rotate about the longitudinal axis thereof.

When the ski is at rest before any of the three measurements of flexural or torsional stiffness is made in accordance with the principles of our invention, the midpoint of the ski and the respective "low points" of the ski just forward of the tail and just aft of the tip are all maintained at the same level. The flexural stiffness of the afterbody and of the forebody of the ski are both measured by deflecting those portions of the ski through an identical predetermined distance, measured at the tail station and the tip station of the apparatus respectively. The torsional stiffness of the forebody of the ski, as modified by forces transmitted through the ski from the afterbody, is measured by deflecting the ski at the tip station by raising one side of the ski and lowering the other side of the ski through a predetermined distance which is identical to the distance used in measuring the flexural stiffnesses of both the forebody and the afterbody of the ski.

The apparatus which permits and facilitates the taking of the aforementioned steps comprises an elongated base, which may be desirably be in the form of a pair of hollow metal cylinders, side by side. Mounted in slidable fashion thereon are a tip station, a center station, and a tail station each of which preferably has at its top a substantially cylindrical roll on which the ski is supported during the aforementioned tests. A pneumatic cylinder having a stroke of fixed distance (typically ten millimeter) forces the tail of the ski upward, permitting measurement of the force necessary to produce that deflection. Similarly, the forebody of the ski is deflected upward by a pair of pneumatic cylinders having a stroke of fixed distance (again typically ten millimeters). Once again, the force necessary to produce the fixed deflection at the point of application thereof is measured. Finally, the measurement of torsional stiffness is accomplished by actuating the cylinders at the tip station in opposite directions, but through equal distances of displacement, thereby twisting the ski substantially about its longitudinal axis.

The forces necessary to accomplish all the aforementioned deflections are measured by a sensing device at the center station of the apparatus. We prefer to employ as the sensing device a pair of load cells, each of which incorporates a strain gate. The bending caused at the load cell in the center station by the application of each of the aforementioned forces is indicated by the strain gages, typically energized by a source of ten volts DC. The output of the strain gages (typically 20/35 millivolts per kilogram of force applied) is fed to a digital output meter, which indicates the force in pounds or in tenths of a pound.

The cylinders that produce the deflection of the ski are desirably powered from a compressor of approximately one-half horsepower capacity. The compressor is connected to the various actuating cylinders through valves connected in the form of "fluid logic" to permit on/off control, selection between tail and tip application of force, and direction of forces applied by the respective cylinders at the tip station.

The hollow cylinders of the base of the apparatus may be employed as a reservoir for the compressed air flowing from the compressor and held in readiness to energize the aforementioned pneumatic cylinders. An instrument panel for mounting the switches that control the compressor and the fluid logic appears on the face of the apparatus within view and control of the operator.

BRIEF DESCRIPTION OF THE DRAWINGS

The invention summarized above will be described in detail in the following specification. The specification will be best understood if read while referring to the accompanying drawings in which.

DESCRIPTION OF THE PREFERRED EMBODIMENTS

Figures 1, 2:
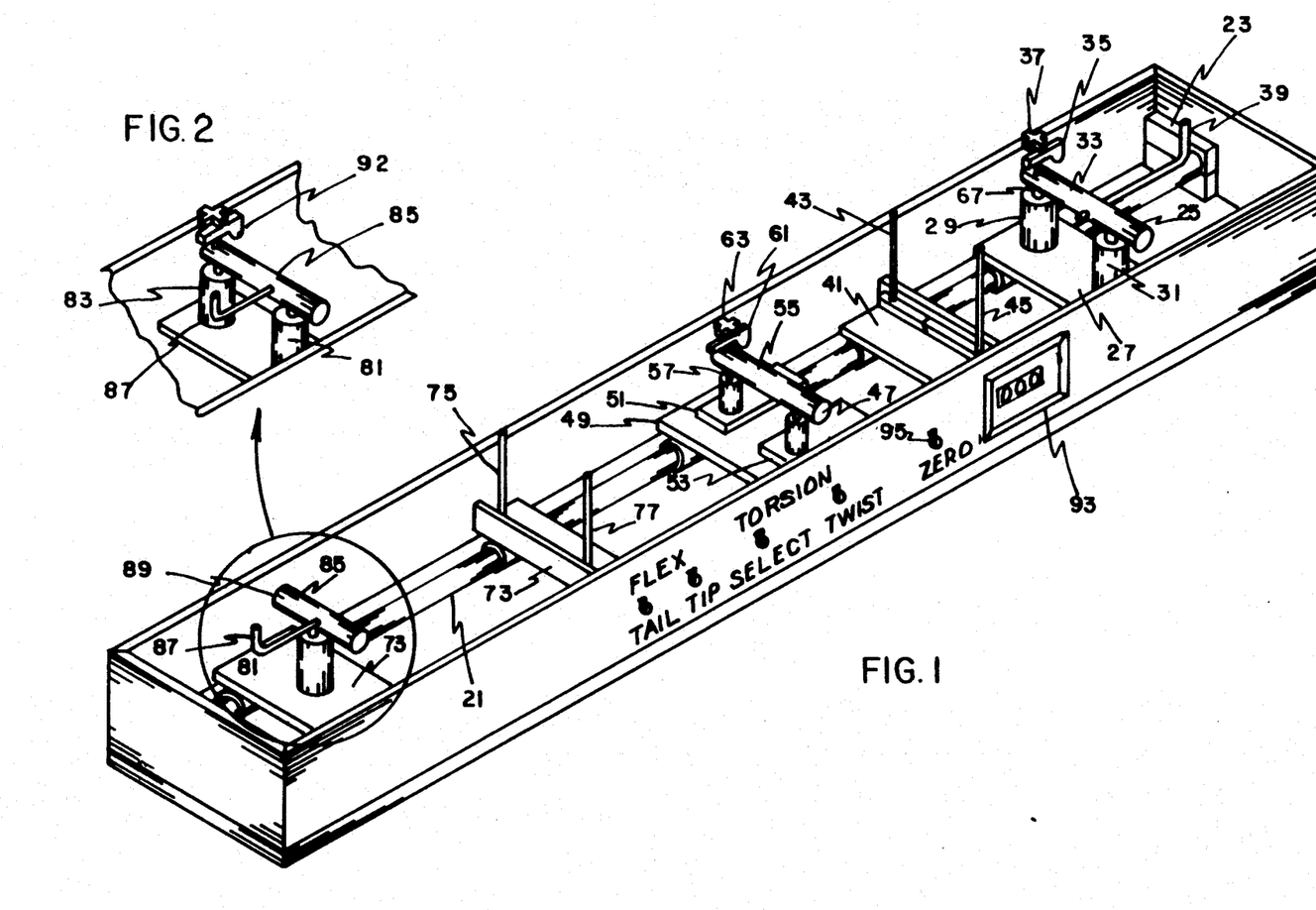
FIG. 1 is a perspective view of the assembled apparatus in accordance with our invention.
FIG. 2 is a perspective view of an alternative version of the sub-assembly of the apparatus in accordance with the invention, the sub-assembly being indicated by a circle in FIG. 1.

Turning to FIG. 1 of the drawings, we see in perspective a representation of the apparatus in accordance with our invention. The apparatus may have a protective cover, but the cover has been removed to permit visualization of the internal components of the apparatus. Preferably, the apparatus is supported by a pair of parallel rails, a first one of which is exemplified by a rail 21 as shown in FIG. 1. A second parallel rail, coextensive to rail 21, is arranged in parallel fashion within the container of the apparatus, but is obscured by the container in FIG. 1. We prefer to form the rails from hollow aluminum tubing, typically 1¼ inch in outside diameter, and having a wall thickness which may be of the order of 0.055 inch. We prefer to employ hollow aluminum tubing of substantial diameter for this purpose because, as will be explained later in this specification, the rails may serve as reservoirs for compressed air which actuates the apparatus of our invention.

Figure 3:
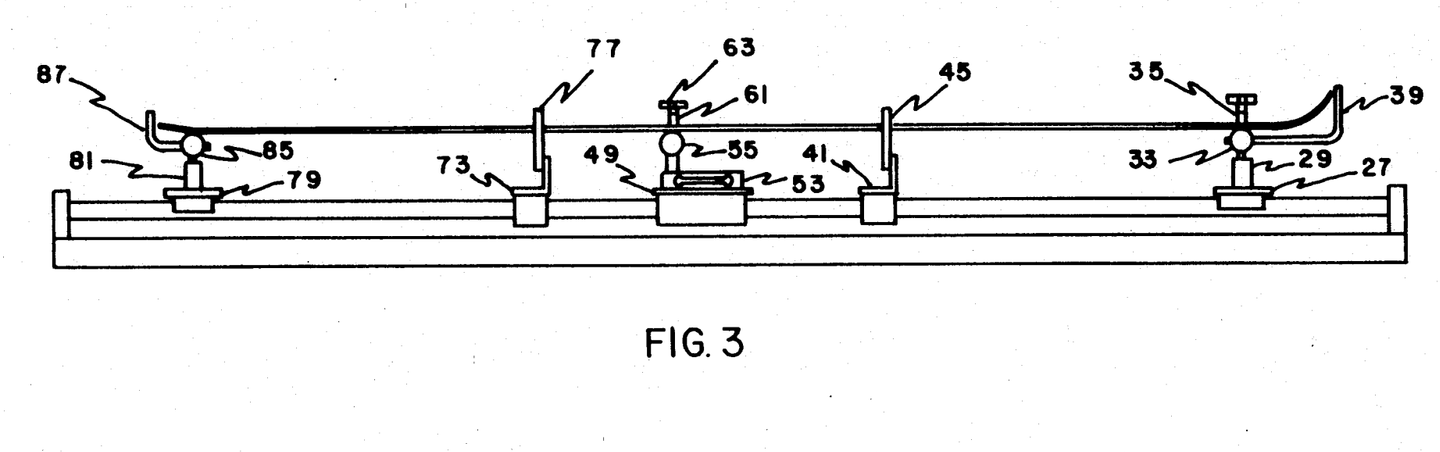
FIG. 3 is an elevation view of the operative components of the assembly in accordance with our invention, showing further a ski in its flattened state positioned atop the apparatus in accordance with the invention, with ski camber forcibly overcome, and ready for flexibility tests of its forebody.

We prefer to support the rails in pairs of blocks such as indicated at 23 in FIG. 1. Each of the pairs of blocks has a semi-circular hole which accommodates the rail seated therein. A pair of blocks is shown at 23, embracing one end of rail 21. It will be understood that each of the rails may be supported by blocks at both ends and intermediate its ends. We favor the use of polypropylene material for blocks such as block 23. The blocks supporting the rails may in turn be supported by a pair of parallel angle irons running longitudinally of the apparatus and spaced apart slightly more widely than the aforementioned rails. For the sake of saving weight, we prefer to employ aluminum right-angle stock, each flange of which is 1¼ inches wide. Near the right-hand end of the apparatus is a tip station 25 which is mounted upon a first platform 27 which is in turn supported at each end by one of the aforementioned rails. Mounted upon first platform 27 are a first pneumatic cylinder 29 and a second pneumatic cylinder 31, each of which is oriented vertically so that its plunger is pointing upward. The respective plungers of first pneumatic cylinder 29 and second pneumatic cylinder 31 support a first roll 33 which is disposed horizontally, and transversely within the apparatus according to our invention. Near one end of first roll 33 is affixed a first clamp 35 having a handle 37 or other means for tightening first clamp 35 over a ski when it is placed in position upon first roll 33 and supported by other rolls of the apparatus as will be seen. Reference to FIG. 3 of the drawings shows the way in which the ski could be tested as mounted in the apparatus according to the invention, with first roll 33 supporting the ski at the low point just aft of the upturned tip, and with the ski clamped in place by first clamp 35. For reasons which will later become apparent, only one edge of the ski need be clamped by first clamp 35, although it would be possible to clamp the entire width of the ski to first roll 33. If skis of various lengths are to be tested in the apparatus according to the invention, tip station 25 may be adjusted in position by sliding first platform 27 along its supporting rails. Having located the position at which first roll 33 contacts the "low point" just aft the tip of the ski, the testing of further skis of the same length may be facilitated by means of a tip fixture 39, which is to be in contact with the very tip of each ski of that length which is to be tested. Tip fixture 39 comprises a piece of stiff material bent in approximately the form of a right angle, one end of which is supported by first roll 33, whereas the other end contacts the tip of the ski to indicate that it is correctly positioned with regard to its longitudinal axis.

We prefer to form first roll 33, and the other rolls of the apparatus, from cylindrical material such as aluminum so that the ski to be tested is in contact with the roll only through a line which is one of the generatrices of the roll and is also a transverse line across the running surface of the ski.

Moving to the left in FIG. 1, we find a centering fixture comprising a second platform 41 mounted at each end upon one of the aforementioned rails in slidable fashion thereon. Second platform 41 supports a first upright 43 and a second upright 45 which are arranged to move simultaneously toward the center line of the apparatus or simultaneously away from the center line of the apparatus as the case may be. By moving first upright 43 and second upright 45 toward each other until they contact the respective edges of the ski mounted in the apparatus for test purposes, the centering fixture insures that the ski is laterally centered on the apparatus.

Moving again to the left in FIG. 1, we encounter a center station 47 supported by a third platform 49 which is in turn carried by the aforementioned parallel rails. Supported upon third platform 49 are a first load cell 51 and a second load cell 53. First load cell 51 and second load cell 53 are connected to a second roll 55 through a first link 57 and a second link 59 respectively. The assembly of center station 47 is completed by a second clamp 61 surmounted by a second handle 63 of clamping the ski to second roll 55 for test purposes. The relationships among the aforementioned components are shown clearly by the elevation view of FIG. 6 and the side view of FIG. 7, for center station 47, just as the relationships among the components of tip station 25 were shown clearly by the elevation view of FIG. 4 and by the side view of FIG. 5.

Figure 4:
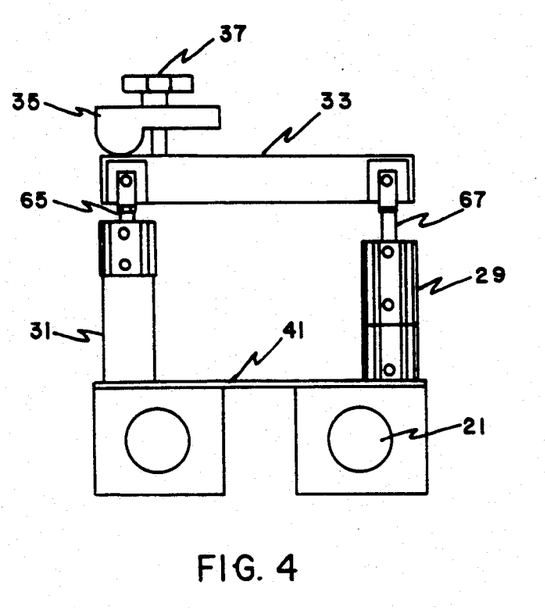
FIG. 4 is an elevation view of a "tip station" in accordance with our invention, looking at said tip station in the direction of the longitudinal axis of the apparatus. If desired, this configuration of tip station may also function as a "tail station" as shown in FIG. 2 of the drawings.
Figure 5:
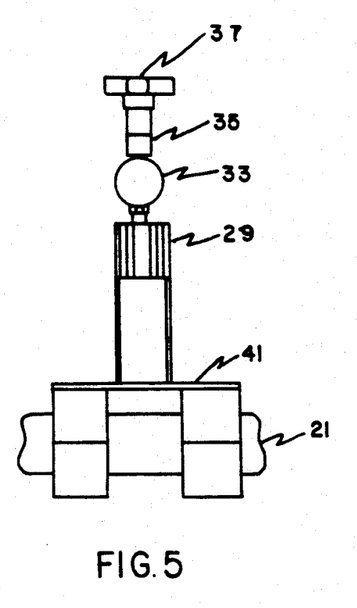
FIG. 5 is an elevation view, taken in a transverse direction, of the tip station of FIG. 4.
Figure 6:
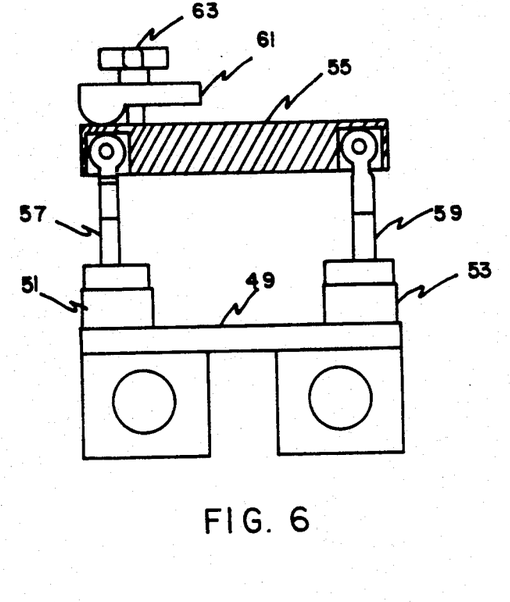
FIG. 6 is an elevation view of a center station of the apparatus in accordance with our invention, taken in the direction of the longitudinal axis of the apparatus.
Figure 7:
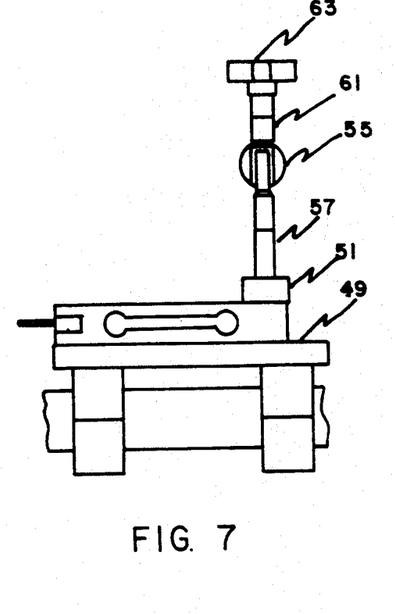
FIG. 7 is a view taken of the center station in accordance with FIG. 6, looking in a direction transverse to the longitudinal axis of the apparatus.

The distinction between the respective functions of the tip station 25, illustrated in FIGS. 4 and 5 of the drawings, on the one hand, and the center station 47, illustrated in FIGS. 6 and 7 of the drawings, will now be apparent. In tip station 25, upward force is applied to first roll 33 through a first piston rod 65 and a second piston rod 67. As will later be explained, the force in one of these piston rods may, if desired, be reversed in order thereby to exert a torque upon the forebody of the ski under test.

Although the forces applied to roll 33 by first piston rod 65 and second piston rod 67 are either both lifting forces or one lifting force and one lowering force, the forces applied to second roll 55 by first link 57 and second link 59 are constrained to be only downward force or forces. This statement will be clarified in connection with the description of the steps to be taken in the practice of the method in accordance with our invention.

Figure 8:
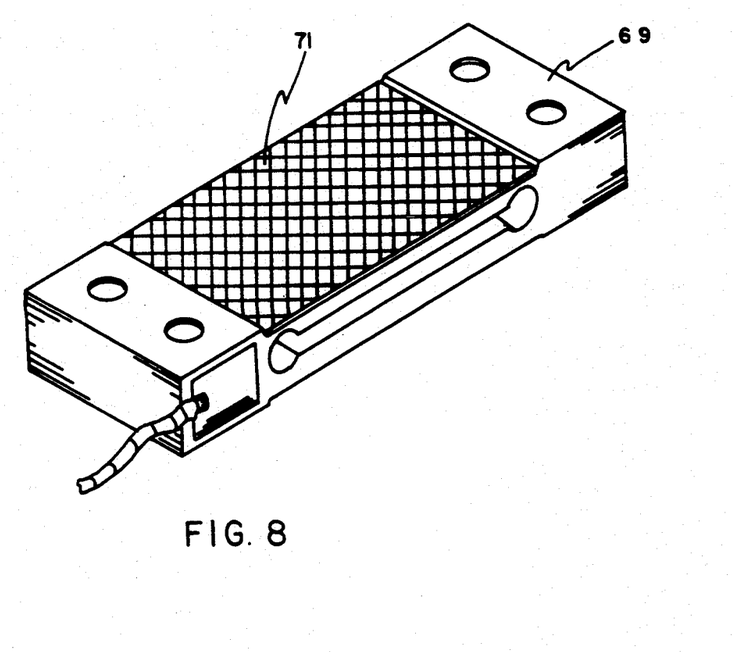
FIG. 8 is a perspective view of one form of load cell which appears in duplicate in the center station in accordance with FIG. 6, for measuring force applied to the ski during the testing process.

At this point, it becomes necessary to explain the nature of first load cell 51 and second load cell 53, end views of which appear in FIG. 6 of the drawings. The nature of first load cell 51 and second load cell 53 will become clear from an examination and explanation of FIG. 8 of the drawings. FIG. 8 is a perspective view of a particular form of load cell which we favor using for the purpose of measuring forces in the testing of skis for flexibility and stiffness. This particular load cell is the SCAIME load cell Model EP-35, manufactured in France by a company of the same name, and distributed in the United States by PTC Electronics, Inc. of Wyckoff, N.J. The rectangular body shown in FIG. 8 is a block of aluminum which has been bifurcated by boring holes through it so that the application of force to the upper side of the parallelpiped will cause it to deflect and move with respect to the lower surface of the aluminum parallelepiped. The application of sufficient force to the surface appearing prominently in FIG. 8 causes bending of that surface. Inset into the surface is a strain gauge of a form well known in the force-measurement art. In a strain gauge, of course, the resistivity and resistance of the strain gauge change with the elongation of the material to which the strain gauge is firmly attached. In particular, the stretching of the strain gauge accompanying the bending of the exposed surface of the load cell increases the electrical resistance of the strain gauge nearly linearly with the force applied to the load cell. Strain gauges are generally calibrated so that the resistance change is measurable with the elongation, rather than compression, of the strain gauge. Thus, it becomes necessary to mount the load cell of FIG. 8 so that the surface shown in FIG. 8 will be elongated by force rather than compressed. Therefore, the aluminum block 69 of the load cell is mounted on third platform 49 in an inverted position so that strain gauge 71 faces downward rather than upward. A force applied to what has become the lower surface of the load cell, through a hole in the load cell, will cause a bending moment in the surface of the load cell bearing the strain gauge so that the strain gauge is placed in tension. Accordingly, upward forces exerted by a second roll 55 through first link 57 and second link 59 on first load cell 51 and second load cell 53 respectively will produce elongations of the strain gauges and consequent increases in resistance, which may be detected in a Wheatstone bridge by well known means. It will soon become apparent why second roll 55 exerts upward forces on first link 57 and second link 59.

It will be understood that first load cell 51 and second load cell 53 may be other than the SCAIME type EP-35, which we happen to favor. However, since we have obtained such satisfactory results with this particular type of load cell, some further particulars thereon will now be given. The load cell is designed for the application and measurement of forces up to 35 kilograms. The strain gauge is energized from a direct-current source of ten volts. The output of the strain gauge is fed through a bridge circuit to a digital meter for which the sensitivity is two millivolts per volt of excitation. Thus, full-scale output of the meter, which may be a digital meter, represents 20 millivolts and is produced when the full load of 35 kilograms force is applied to the load cell.

As will later be seen, the forces applied by second roll 55 to first link 57 and second link 59 may, upon occasion, be unbalanced. Therefore, we favor coupling first link 57 and second link 59 to second roll 55 through ball and socket joints in order that any rocking motion of second roll 55 may not cause binding with the links or the exertion of a force in a direction other than along the axes of the respective links.

Having described in some detail the structure of center station 47, we shall now complete the description of the remaining components of the apparatus according to the invention and as shown in assembled form in FIG. 1 of the drawings. Moving to the left from center station 47, we find a fourth platform 73, upon which are mounted a third upright 75 and a fourth upright 77. Once again, third upright 75 and fourth upright 77 are disposed upon fourth platform 73 in such a way that they can move simultaneously toward each other and toward the center line of the apparatus or can move simultaneously away from each other and away from the center line of the apparatus. Thus, they may be pushed inward to embrace the respective edges of the ski that is supported upon the apparatus. That insures that the afterbody of the ski is centered on the apparatus, just as first upright 43 and second upright 45 insured that the forebody of the ski is centered on the apparatus. Reference to FIG. 3 illustrates the manner in which third upright 75 and fourth upright 77 bear against the respective edges of the ski under test.

Proceeding again to the left in the assembly of FIG. 1, we find a fifth platform 79 supported upon the aforementioned parallel rails in a slidable fashion thereon. Fifth platform 79 supports a third pneumatic cylinder 81 and, if desired, a fourth pneumatic cylinder 83 as shown in FIG. 2 of the drawings, representing an alternative to the configuration of the tail station shown in FIG. 1. Mounted atop the piston rod of third pneumatic cylinder 81 or atop the respective piston rods of third pneumatic cylinder 81 and fourth pneumatic cylinder 83 is a third rod 85, positioned transversely of the apparatus according to the invention. Once again, we prefer that third roll 85, like first roll 33 and second roll 55, be cylindrical in configuration and formed from a material such as aluminum. The purpose of third roll 85 is to support the ski at the low point which is present in most skis just forward of the tail of the ski. The longitudinal positioning of the ski in the apparatus is aided by a tail fixture 87 which comprises a stiff member extending rearwardly, and then upwardly in the form of a substantially right-angle bend, from third roll 85. Thus, tail fixture 87 cooperates with tip fixture 39 in positioning the ski longitudinally for testing. Once gain, the objective is to position the ski so that first roll 33 supports the ski at the low point aft the tip, while third roll 85 supports the ski at the low point just forward of the tail of the ski. Of course, tip fixture 39 and tail fixture 87 are adjustable in the respective rolls which support them. Moreover, the rolls themselves as component parts of tip station 25 and of tail station 89 may be adjusted in position on the parallel rails that support the respective platforms on which they are mounted.

Having described the principal structural components which comprise the apparatus in accordance with our invention, we are now ready to explain the steps that comprise the method in accordance with our invention. As has already become apparent, the first step in the practice of the method is to place on the apparatus, as just described, the ski to be tested for stiffness and flexibility, flexural or torsional, or both. The next step is to clamp the ski firmly in place upon the rolls which have been supplied for the support of the ski near its mid-point, just aft of its tip, and just forward of its tail. As is well known, most skis have a built-in "camber," which means that, as the ski is placed on a flat surface, the mid-point of the ski will be somewhat above the surface unless it is constrained to contact the surface by applying a force to the ski. The amount of camber at the mid-point of the ski varies from ski to ski but is ordinarily within the range of of ½ inch to ¾ inch. Having clamped the ski in place by setting first clamp 35 and second clamp 61 and, if the variant of FIG. 2 is employed, by setting a third clamp 91, it is of interest to measure the amount of force required to hold the mid-point of the ski in contact with second roll 55 supporting the mid-point of the ski. It will be understood that first roll 33 and second roll 55 and third roll 85 are all at the same level and perfectly aligned with one another. Thus, a ski having camber, if supported at the low points by first roll 33 and third roll 85, would not come in contact with second roll 55 unless constrained to do so by second clamp 61. We prefer to start the tests from the position in which the ski is clamped, at least to first roll 33 and second roll 55. Furthermore, we prefer to measure the force exerted by second roll 55 on first link 57 and second link 59 in order to produce the aforementioned flattening of the ski body. The electrical resistances of the strain gauges in load cells 51 and 53 form part of an electrical bridge across certain arms of which voltages may be measured. When the ski has been "flattened" as aforementioned, we prefer to adjust the remaining resistances in the bridge so that the output of the meter is brought to zero. In FIG. 1 of the drawings, a digital meter 93 and a switch for adjusting or "zeroing" the resistance bridge are indicated by the reference 95. The next step which we customarily take in the testing of a ski is to measure the flexural elasticity or stiffness of the afterbody of the ski. As aforementioned, no effort is made, in the practice of the method of our invention, to isolate the flexural stiffness of the afterbody from forces that may be transmitted through the waist of the ski to the afterbody from the forebody of the ski. We believe that such a type of measurement is realistic because, after all, the ski is not clamped when it is in use. For that reason, we prefer the method according to our invention over the method set forth in the aforementioned test standards of the American Society for Testing and Materials.

In measuring the flexural stiffness of the afterbody of the ski, we cause the third roll 85 of tail station 89 to move upward through a distance of 10 millimeters. We do this by energizing third pneumatic cylinder 81, which has a stroke of ten millimeters and can therefore cause deflection of the tail of the ski by a like amount. If the variation of configuration of tail station 89, as illustrated in FIG. 2 of the drawings, is employed, then both third pneumatic cylinder 81 and fourth pneumatic cylinder 83 are energized so as to raise third roll 85 through a distance of 10 millimeters. In order to understand the way in which the aforementioned deflection of the afterbody of the ski is attained, we must refer to FIGS. 9 through 11 of the drawings. These figures illustrate in a schematic fashion the pneumatic circuitry comprising the pneumatic cylinders and their control valves. It should be mentioned at the outset that, although we prefer to produce the deflection of the ski by pneumatic means, it would be possible to employ electro-magnetic means, such as solenoids, to raise first roll 33 and third roll 85 to produce the deflections desired.

Figure 9:
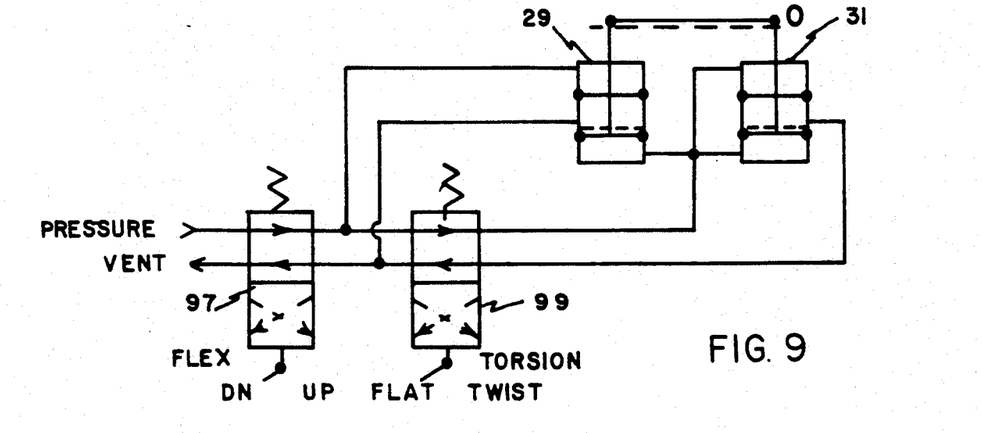
FIG. 9 is a schematic diagram of the pneumatic circuitry showing two pneumatic cylinders of the tip station of FIG. 5, together with a pair of four-way pneumatic valves which control the operation of the pneumatic cylinders. The positions of the pneumatic cylinders and their control valves are as they would be when a ski has been flattened for tests but has not had any other deflecting or torsional force applied thereto.
Figure 10:
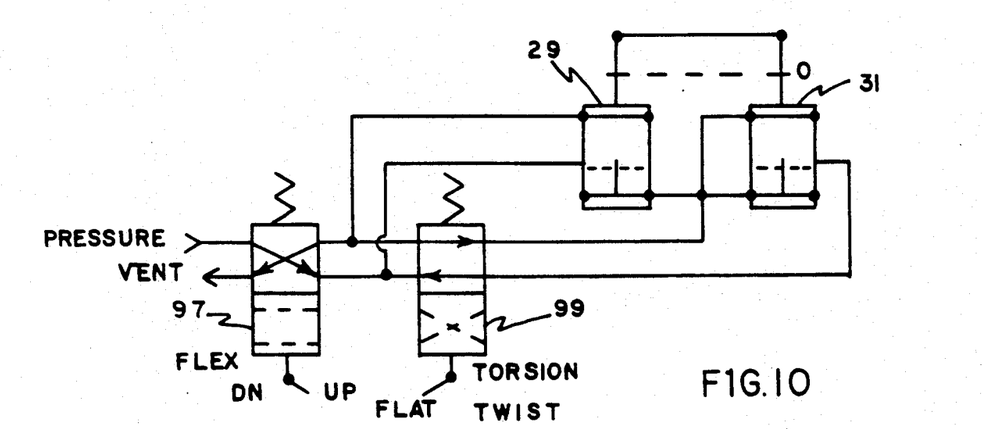
FIG. 10 is a schematic view of the same pneumatic cylinders and their pneumatic control valves in which the settings are such as to apply flexural forces to deflect the tip of the ski upward.
Figure 11:
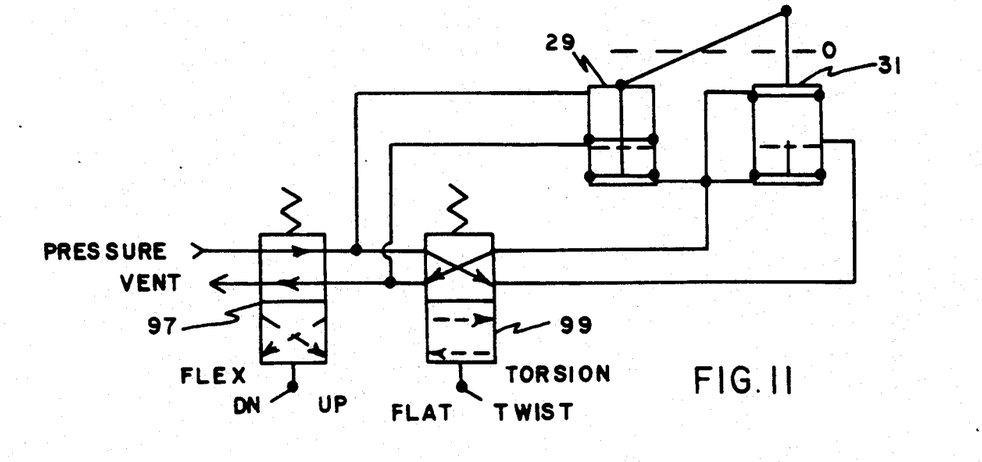
FIG. 11 is a schematic diagram of the same pneumatic cylinders and control valves in which the positions of the valves and of the pistons in the cylinders are such as they would occupy when torsional force is being applied to the ski to test its torsional elasticity.

FIGS. 9 through 11 illustrate the progressive change of state of the pneumatic circuits as we proceed through the various steps of the method in accordance with our invention. The last step of the method involves the measurement of torsional stiffness. Inasmuch as we are primarily concerned with the torsional stiffness of the forebody of the ski, rather than the afterbody of the ski, let us assume that the pneumatic circuitry illustrated in FIGS. 9 through 11 is that of the tip station 25 of our apparatus. In that even, first pneumatic cylinder 29 and second pneumatic cylinder 31 are shown as indicated in all three of the FIGS. 9 through 11. We prefer to employ pneumatic cylinders in which the pistons may selectively occupy any of three different positions within the main portion of each cylinder. It will be understood that the position of the piston in the main cylinder is determined by the input pneumatic pressures which bear not only on the upper and lower surfaces of the main piston but also upon the upper and lower surfaces of the auxiliary piston in the auxiliary cylinder. Latter has a piston rod that penetrates the membrane between the main cylinder and the auxiliary cylinder so that the end of the piston rod can impede the motion of the main piston within the main cylinder but cannot attract it. Such valves are available from companies such as SMC Corporation and are widely sold in the marketplace. It will be understood that the main piston, moving in the main cylinder, is coupled through its piston rod to the roll, such as first roll 33 in FIG. 1.

When the apparatus in accordance with the invention is at rest, but the ski has been flattened and the resistance bridge leading to the output meter has been "zeroed," the setting of the control valves in the pneumatic circuit is as shown schematically in FIG. 9 of the drawings.

In FIG. 9 of the drawings, pneumatic pressure is supplied from a source to a first control valve 97 and a second control valve 99, from which the air under pressure is in turn fed to first pneumatic cylinder 29 and second pneumatic cylinder 31 in accordance with the settings of the aforementioned control valves. Similarly, the air from first pneumatic cylinder 29 and second pneumatic cylinder 31 is vented through control valves 97 and 99 as shown schematically in accordance with the settings of those respective valves.

The control valves that we prefer to employ are operated manually by means of a switch for each of the valves. Those switches are shown schematically in FIGS. 9 through 11 of the drawings, and are represented on the control panel of the apparatus as illustrated in FIG. 1 of the drawings. When the "flex" switch of first control valve 97 is in that "down" position, the air pressure and the vented air pass straight through that control valve as indicated schematically in FIG. 9. Likewise, when the switch of second control valve 99 is set in the "flat" position, air passes through second control valve 99 in such a way that either the pistons of first pneumatic cylinder 29 and second pneumatic cylinder 31 are in their neutral positions or they both are in the "up" position. With that setting of second control valve 99, there is no possibility of opposite motions of the pistons of the two pneumatic cylinders so as to produce a twisting of first roll 33 and a torsional deflection of the ski.

If the "flex" switch of first control valve 97 is moved to the "up" position, while the "torsion" switch of second control valve 99 is maintained in the "flat" position, a "crossover" of connections takes place in first control valve 97, thereby admitting air under the main pistons of both first pneumatic cylinder 29 and second pneumatic cylinder 31 and causing them to raise first roll 33, thereby deflecting the ski upward and causing a tension in first link 57 and second link 59 of the center station.

Once again, tension in those links applies stress to the load cells of center station 47 and permits a measurement in effect of the force that was necessary to move first roll 33 upward through a distance of 10 millimeters.

Returning to the steps of the method in accordance with our invention, it has been stated that the first step after zeroing the meter is to measure the force necessary to deflect the afterbody of the ski upward to a distance of 10 millimeters. If the alternate configuration of the tail station, as illustrated in FIG. 2 of the drawings, is employed, the foregoing discussion of and explanation of the operation of the fluid logic, including the valves and cylinders, is directly applicable. It may be explained that the alternative configuration of tail station as illustrated in FIG. 2 is a replica of the configuration employed in tip station 25.

Upon measurement of the force required to produce 10 millimeters deflection in the tail station, the force is released by returning the fluid logic to the condition illustrated in FIG. 9. Thereupon, the next step of the test method may be taken. That step is normally to measure the flexural stiffness or flexibility of the forebody of the ski. That step has already been explained in connection with the discussion of the changes in the pneumatic circuitry that are necessary to govern the operation of first pneumatic cylinder 29 and second pneumatic cylinder 31.

It would be possible to have a configuration of apparatus in which first pneumatic cylinder 29 and second pneumatic cylinder 31 had a pair of control valves for themselves, whereas third pneumatic cylinder 81 and fourth pneumatic cylinder 83 had another pair of control valves for their own accommodation. However, such duplication is not necessary because proper switching can enable first control valve 97 and second control valve 99 to service the pneumatic cylinders of both the tip and tail stations. Accordingly, a selector switch for measurements of flexural deflection is shown on the panel illustrated in FIG. 1 of the drawings. Either the "tail" or the "tip" switch may be depressed for flexural measurements upon the ski, depending upon whether the afterbody or the forebody of the ski is to be tested.

The next step in the test procedure is to reset the valves to the condition of FIG. 9 so that the ski resumes its initial undeflected position, except that, as aforementioned, the camber of the ski remains suppressed.

The next step in the procedure is that of measurement of the torsional flexibility or stiffness of the forebody of the ski. That is accomplished by setting the "flex" switch of first control valve 97 in the "down" position, while setting the "torsion" switch of second control valve 99 in the "twist" position. As shown in FIG. 11 of the drawings, that setting of the switches causes the piston of first pneumatic cylinder 29 to be depressed and the piston of second pneumatic cylinder 31 to be raised upward to the full extent of its travel. Thus, as illustrated in FIG. 11, the main piston of first pneumatic cylinder 29 has moved downward from its neutral position through a distance of 10 millimeters, while the main piston of second pneumatic cylinder 31 has moved upward from its neutral position by a similar distance of 10 millimeters. Once again, pneumatic cylinders of the SMC type are capable of such operation as just described. It is to be noted that a "crossover" has taken place in second control valve 99 in order to produced the "push-pull" force that causes torsional deflection of the ski. Control valves marketed by the ADI Corporation are suitable for this type of service.

The final step of the test procedure, after having noted the forces necessary to produce the deflections of 10 millimeters by both first pneumatic cylinder 29 and second pneumatic cylinder 31, is to reset the "torsion" switch of second control valve 99 to the "flat" position, thereby causing the condition of FIG. 9 to be resumed. As aforementioned, if it is desired to measure the torsional stiffness and flexibility of the afterbody of the ski, the "flex" switches may be set by depressing the "tail" switch, in order to cause differential actuation of third pneumatic cylinder 81 and fourth pneumatic cylinder 83. However, it is generally the forebody of the ski which is of interest so far as the measurement of torsional flexibility and stiffness are concerned.

The forces necessary to produce a 10 millimeter deflection of the afterbody or the forebody of a ski or to cause a similar deflection upward of one edge of the ski concurrently with a similar downward deflection of the other edge of the ski are generally not very large. Therefore, if they were measured in pounds, the numbers would be very small. Accordingly, we prefer to calibrate our output digital meter so that it reads in tenths of a pound, thereby producing numbers that are easy to record and visualize. When we are preparing a pair of skis for sale, we prefer to measure first the force necessary to overcome the camber and then to measure the force necessary to produce the tail deflection, and then subsequently to measure the force necessary to produce the tip deflection, and finally to measure and record the forces necessary to produce the torsional deflection as mentioned. We record the numbers for all four of these measurements and we prefer that the buyer of the pair of skis return them for remeasurement in a period of about a year. If the corresponding measurements after a year of use are significantly different, it may be that the skis have become "soft" and that they should be replaced. These measurements also show whether, with the passage of time, a properly mated pair of skis remains properly mated or whether one of them has changed in its characteristics so that it is no longer a satisfactory mate to the other ski.

Early in the specification, it was noted that rail 21, and its parallel mate, were preferably formed of hollow aluminum tubing having a substantial diameter. The purpose of such configuration, aside from saving weight, is to provide a reservoir for compressed air which is led to the pneumatic cylinders to actuate them. We prefer to supply air to the cylindrical reservoirs, and thence to the control valves and pneumatic cylinders, at a pressure between 60 and 110 pounds per square inch. Air under such pressure may conveniently be supplied by a compressor driven by a motor of approximately ½ HP.

The electrical connections of the circuitry for reading out the voltages generated by the load cells are a matter of personal choice. However, we prefer to connect the strain gauges of the two load cells in parallel in a resistance bridge for measurement of force when the skis are being tested for flexural deformation. Connecting the strain gauges thus in parallel effectively produces an averaging of the outputs of the two respective load cells. When torsional measurements of the ski are being taken, we presently prefer to measure only the output of the load cell in which the strain gauge is in tension, while bypassing the output of the load cell for which the strain gauge is in compression by virtue of the twisting forces.

It has been mentioned that the requisite deflections of the ski under test could be produced by electro-magnetic or mechanical means rather than by pneumatic means. Such a usage would involve the adoption of solenoids or cams in place of pneumatic cylinders. For various reasons, it is our preference to employ pneumatic circuitry and actuators in the apparatus in accordance with our invention. However, we do know that various changes may be made in the apparatus and method in accordance with this disclosure. The disclosure sets forth fully the most-favored embodiment of our invention known to us at the time of filing of the application thereon. Recognizing that certain changes therein may be made by others without departing from the scope of the invention, we set forth our invention in the the following claims which, with their equivalents, are desired to be secured hereby.

What we claim as new and desire to secure by Letters Patent of the United States is:

1. A ski tester for measuring flexural and torsional stiffness of a ski having a top surface and a running surface, a forward tip and a rearward tail, said ski tester comprising:
   (a) an elongated base having a length at least equal to that of the ski to be tested,
   (b) a tail station mounted on said base for supporting said ski at a location in its afterbody, said tail station having first controllable means for applying force to the running surface of said afterbody of said ski to deflect flexurally said afterbody through a predetermined distance, measured at said tail station,
   (c) a center station mounted on said base for supporting said ski at a location in its mid-portion, said center station having central clamping means for releasably holding the mid-portion of said ski in firm contact with said center station,
   (d) a sustaining tip station mounted on said base for supporting said ski at a location in its forebody, said sustaining tip station having second controllable means for applying force to the running surface of said forebody of said ski to deflect flexurally said forebody through a predetermined distance, measured at said tip station, said second controllable means including first and second controllable portions for applying force to left and right sides of said ski respectively in the same directions with respect to the running surface of said ski and also for applying force to left and right sides of said ski respectively in opposite directions with respect to the running surface of said ski to deflect torsionally said forebody, and
   (e) means for measuring the force exerted by said first controllable means when it has deflected flexurally said afterbody through a predetermined distance, means for measuring the force exerted by said second controllable means when it has deflected flexurally said forebody through a predetermined distance, and means for measuring the respective forces exerted by said first and second controllable portions of said second controllable means when they have deflected torsionally said forebody by each acting through a predetermined distance.

2. A ski tester in accordance with claim 1 in which said first controllable means in said tail station includes at least one pneumatic cylinder.

3. A ski tester in accordance with claim 2, further including a compressor for supplying compressed air to said first controllable means.

4. A ski tester in accordance with claim 1 in which said second controllable means in said sustaining tip station includes two pneumatic cylinders.

5. A ski tester in accordance with claim 4, further including a compressor for supplying compressed air to said second controllable means.

6. A ski tester in accordance with claim 1 in which said means for measuring the force includes at least one strain-gage device.

7. A ski tester in accordance with claim 1 in which said means for measuring the respective forces includes first and second strain-gage devices, adapted to measure forces respectively exerted in opposite directions.

8. A ski tester in accordance with claim 1, further including at least one means for laterally centering a ski atop said tail station, said center station, and said tip station.

9. A ski tester in accordance with claim 1, further including at least one fixture for longitudinally positioning a ski atop said tail station, said center station, and said tip station.

* * * * *